United States Patent [19]

Maffrand et al.

[11] Patent Number: 4,496,568
[45] Date of Patent: Jan. 29, 1985

[54] ANTIINFLAMMATORY THIENO [2,3-C]PYRIDINE DERIVATIVES

[75] Inventors: Jean-Pierre Maffrand; Daniel Frehel, both of Toulouse, France

[73] Assignee: PACOR, Paris, France

[21] Appl. No.: 487,355

[22] Filed: Apr. 25, 1983

[30] Foreign Application Priority Data

Dec. 19, 1977 [FR] France ................ 77 38308

[51] Int. Cl.³ ............ A61K 31/44; C07D 495/04
[52] U.S. Cl. .................... 514/301; 546/114
[58] Field of Search ............ 546/114; 424/256

[56] References Cited

U.S. PATENT DOCUMENTS 3,845,065 10/1974 Shen et al. ............ 546/114
3,983,125 9/1976 Amselem ............ 546/114
4,065,459 12/1977 Heymes et al. ............ 546/114

OTHER PUBLICATIONS

Maffrand, J. et al., *J. Het. Chem.*, 13, 1347 (1976).
March, J., *Advanced Organic Chemistry*, McGraw Hill, New York, 1968, pp. 745, 728–733.
Hodgman, C. (editor), *Handbook of Chemistry and Physics*, 44th ed., Chemical Rubber Pub. Co., Cleveland, 1961, pp. 564–565.
House, H., *Modern Synthetic Reactions*, W. A. Benjamin, New York, 1965, pp. 78–81.

*Primary Examiner*—Richard A. Schwartz
*Attorney, Agent, or Firm*—Weiser & Stapler

[57] ABSTRACT

This invention relates to a process for the preparation of antiinflammatory thieno [2,3-c]- and [3,2-c]pyridines having respectively the following formulae:

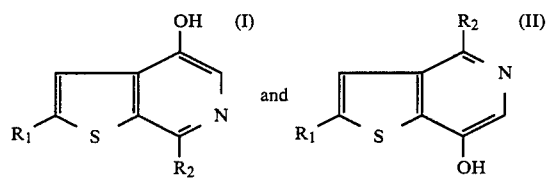

in which $R_1$ and $R_2$, which may be the same or different, represent each a hydrogen atom or an alkyl group, and their pharmaceutically acceptable acid addition salts, comprising:

(a) condensing a compound of the following formulae (VII) or (VIII), respectively,

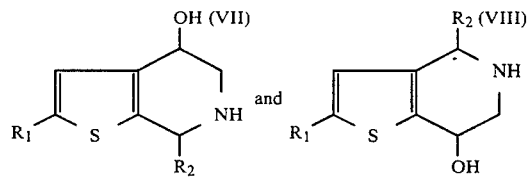

with a sulfonyl chloride having the formula $ClSO_2R_3$, in which $R_3$ is a lower alkyl radical or a phenyl radical optionally substituted with a halogen atom or a lower alkyl group, within a two-phase solvent system and in the presence of sodium carbonate;

(b) oxidizing in a solvent medium the resulting alcohols having respectively the following formula (V) or (VI):

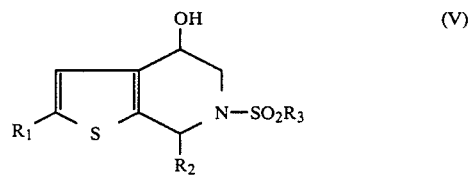

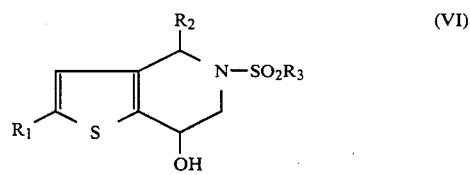

(c) treating the resulting ketones, having the following formula (III) or (IV):

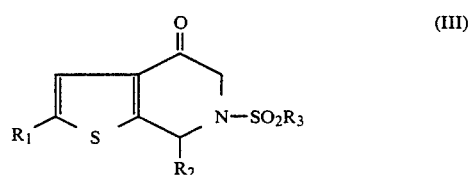

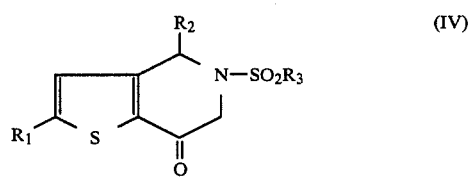

with a basic agent having the formula $RO^-M^+$ in which R is a branched- or straight-chain aliphatic alkyl radical and $M^+$ is an alkali metal cation, within an alcohol solvent having the formula ROH, and at the reflux temperature of the reaction mixture, to give the compounds of the formula (I) or (II), respectively.

21 Claims, No Drawings

ANTIINFLAMMATORY THIENO [2,3-C]PYRIDINE DERIVATIVES

This is a continuation of application Ser. No. 968,785, filed Dec. 12, 1978, now abandoned.

This invention relates to a new process for the preparation of thieno-pyridine derivatives, to the new compounds thus obtained and to their application to warm-blooded animals in human and veterinary medicine.

Said new derivatives are also useful intermediates in the synthesis of compounds useful both in the chemical and pharmaceutical industries.

Thieno-[3,2-c]pyridine derivatives unsubstituted at 4-position, their therapeutic applications, typically as anti-inflammatory agents, and methods for their preparation are already known from U.S. Pat. No. 3,845,065.

This invention relates to a new process for the preparation of thieno-[2,3-c]- and -[3,2-c]-pyridine having respectively the following formulae (I) and (II)

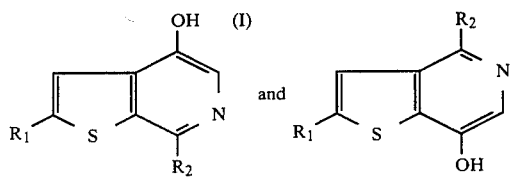

in which $R_1$ and $R_2$, which may be the same or different, represent each a hydrogen atom or an alkyl group, and their pharmaceutically acceptable acid addition salts, comprising:

(a) condensing a compound of the following formula (VII) or (VIII), respectively,

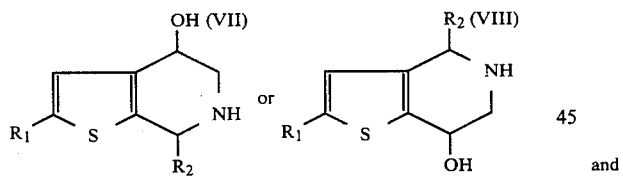

with a sulfonyl chloride having the formula $ClSO_2R_3$, in which $R_3$ is a lower alkyl radical or a phenyl radical optionally substituted with a halogen atom or a lower alkyl group, within a two-phase solvent system and in the presence of sodium carbonate;

(b) oxidizing in a solvent medium the resulting alcohols having respectively the following formula (V) or (VI):

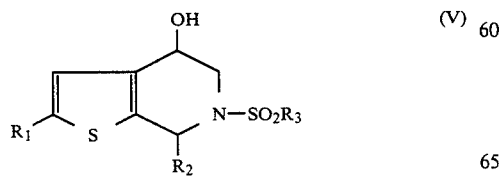

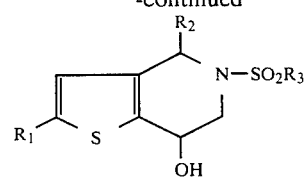

(c) treating the resulting ketones, having the following formula (III) or (IV)

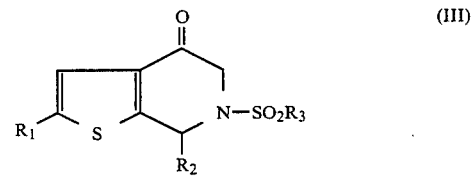

or

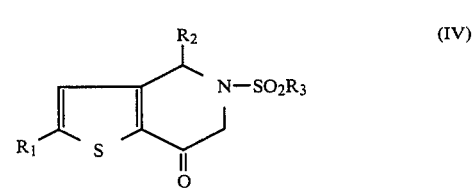

with a basic agent of the formula $RO^-M^+$ in which R is a branched or straight-chain aliphatic alkyl radical and $M^+$ is an alkali metal cation, in an alcohol solvent having the formula ROH and at the reflux temperature of the reaction mixture, to give, respectively, the compounds of the formula (I) or (II).

General formulae (I) and (II) may also be represented under their zwitterion form:

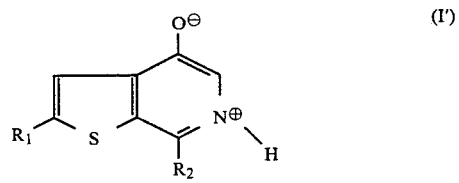

and

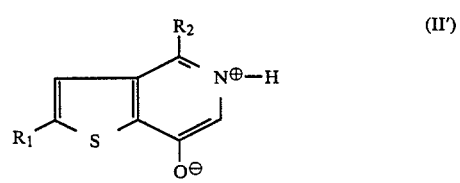

The groups $R_1$ and $R_2$ are typically $C_{1-6}$ lower alkyl groups, such as methyl, for example.

This invention relates also to thieno-[2,3-c]pyridine derivatives having the following formula:

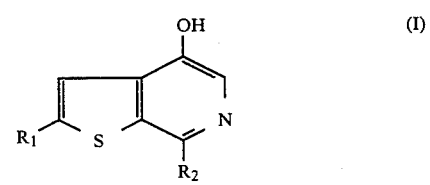

in which $R_1$ and $R_2$, which may be the same or different, represent each a hydrogen atom or an alkyl group, and their pharmaceutically acceptable acid addition salts.

The essential step of the preparation process described above comprises treating with a basic agent a derivative having following formula (III) or (IV):

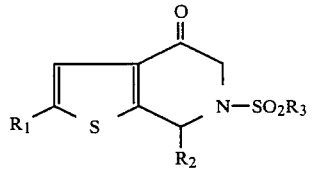
(III)

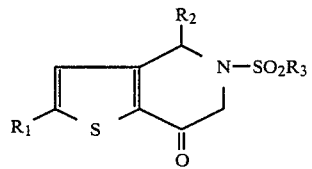
(IV)

in which $R_1$ and $R_2$ have the aforementioned meanings and $R_3$ is a lower alkyl radical, preferably a methyl group, or a phenyl radical optionally substituted with a halogen atom or a lower alkyl group such as a methyl group. The reaction comprises splitting off a sulfinic acid as its $R_3SO_2^-M^+$ salt, under the influence of an alkoxide $RO^-M^+$, according to the following scheme:

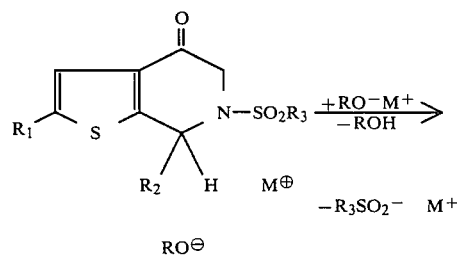

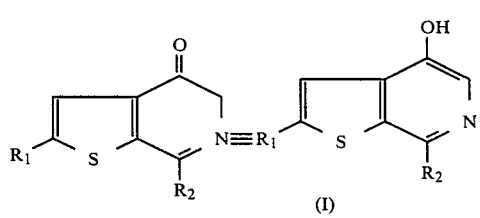
(I)

Similarly, treatment of the compound of the formula (IV) gives the compound of the formula (II).

This reaction is carried out by refluxing in a branched- or straight-chain $C_{1-5}$ aliphatic alcohol ROH, in the presence of its sodium or potassium alkoxide ($RO^-Na^+$ or $RO^-K^+$). The use of potassium tert-butoxide in tert-butanol is particularly advantageous.

Compounds (III) and (IV) are obtained by oxidation of the corresponding alcohols (V) and (VI):

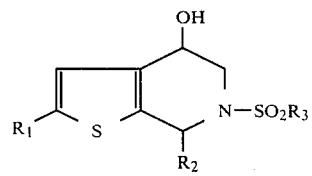
(V)

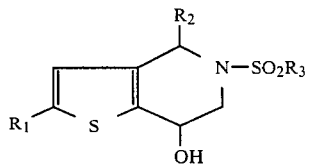
(VI)

The reaction is effected in acetone, using a solution of chromic anhydride in sulfuric acid as oxidizing agent.

Alcohols (V) and (VI) are in turn prepared by condensing corresponding 4,5,6,7-tetrahydro-thienopyridines (VII) and (VIII) with a sulfonyl chloride $ClSO_2R_3$.

$$\underset{(VII)}{\text{[structure]}} \xrightarrow{ClSO_2R_3} (V);$$

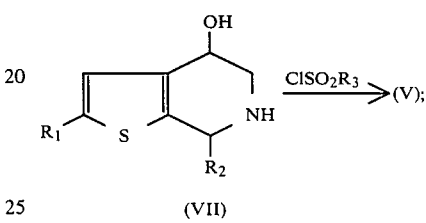

(VIII)

The reaction is effected in a two-phase water-chloroform system, in the presence of sodium or potassium carbonate.

The derivatives (V) and (VI) in which $R_1=R_2=H$ and $R_3=$p-tolyl, have already been mentioned in the literature by J. P. Maffrand & F. Eloy; J. Het. Chem. 1976, 13, 1347.

The starting materials (VII) and (VIII) in which $R_1=H$ are described in the above reference, or in Applicant's U.S. Pat. No. 3,983,125.

An example of the preparation of derivative (VII) in which $R_1=CH_3$ is given in the present disclosure.

Preparation of 4-hydroxy-2-methyl-4,5,6,7-tetrahydrothieno[2,3-c]pyridine: (VII); $R_1=CH_3$; $R_2=H$ A mixture of 5-methyl-thiophene-2-carboxaldehyde (30 g; 0.237 mole) and aminoacetaldehyde dimethylacetal (27.4 g; 0.261 mole) in benzene (250 ml) is refluxed for 2 hours in a flask provided with a Dean-Stark water separator with overhead condenser. After evaporating to dryness, the residue is dissolved in ethanol (250 ml). Sodium borohydride (13.5 g; 0.355 mole) is added portionwise, and the resulting material is left aside overnight at room temperature. Excess sodium borohydride is destroyed by addition of acetone and the mixture is evaporated to dryness. The residue is taken up into water and extracted with methylene chloride. The organic extracts are dried over sodium sulfate and evaporated to dryness. The resulting residual oil is distilled under reduced pressure; b.p.$_2$=127° C.; Yield: 90% The resulting N-(5-methyl-2-thienyl)methyl aminoacetaldehyde dimethylacetal is heated at 60° C. for 1 hour in 6N hydrochloric acid (250 ml). After evaporating to dryness, the residue is triturated with acetone. The off-white crystals of the desired hydrochloride are recrystallized from acetonitrile; M.p.=120° C. Overall yield: 61%.

The following non-limiting Examples illustrate the present invention.

EXAMPLE 1

Preparation of 7-hydroxy-thieno[3,2-c]pyridine

Derivative No. 1; (II); $R_1=R_2=H$ (a) Preparation of 7-hydroxy-5-tosyl-4,5,6,7-tetrahydro-thieno[3,2-c]pyridine (VI): $R_1=R_2=H$; $R_3=$p-tolyl To a mixture of 7-hydroxy-4,5,6,7-tetrahydro-thieno[3,2-c]pyridine hydrochloride (45 g; 0.234 mole), chloroform (100 ml) and saturated aqueous potassium carbonate solution (150 ml) is added dropwise, at room temperature and under vigorous mechanical stirring, a solution of p-toluenesulfonyl chloride (45 g; 0.234 mole) in chloroform (250 ml) and stirring is continued for a further 4 hours. After decantation, the chloroform phase is washed with water, dried over anhydrous sodium sulfate and evaporated to dryness. The residue is purified by column chromatography (silica; eluent: toluene-ethyl acetate 7:3) and recrystallized from isopropanol. White crystals; M.p.=120° C.

Yield: 74%.

(b) Preparation of 7-oxo-5-tosyl-4,5,6,7-tetrahydrothieno[3,2-c]pyridine (IV): $R_1=R_2=H$; $R_3=$p-tolyl Jones' reagent (28.4 ml; 2.50M solution of chromic anhydride in 8.35N sulfuric acid) is added to a solution of 7-hydroxy-5-tosyl-4,5,6,7-tetrahydro-thieno[3,2-c]pyridine (20.3 g; 0.064 mole) prepared as described in (a), in acetone (250 ml). Stirring is continued for a further 2 hours at room temperature, after which the precipitated inorganic salts are filtered off, the filtrate is evaporated to dryness and the residue is taken up into methylene chloride. The organic phase is washed with a 5% aqueous sodium bicarbonate solution and then with water, after which it is dried over sodium sulfate and evaporated to dryness. The solid residue is recrystallized from benzene. Cream coloured crystals; M.P.=174° C.; Yield; 79%.

(c) Preparation of 7-hydroxy-thieno[3,2-c]pyridine (II) $R_1=R_2=H$. Derivative No. 1

A solution of 7-oxo-5-tosyl-4,5,6,7-tetrahydro-thieno[3,2-c]pyridine (19.6 g; 0.064 mole; obtained in (b) above) and potassium tert-butoxide (28.6 g; 0.255 mole) in tert-butanol (300 ml) is refluxed for 2 hours under a nitrogen atmosphere. Evaporation of the solvent in vacuo leaves a residue which is taken up into 2N hydrochloric acid. The aqueous phase is extracted with ether, made basic by addition of concentrated ammonia, and evaporated to dryness. The residue is extracted four times with boiling ethyl acetate. The organic extracts are filtered through a silica bed and evaporated to dryness. The solid residue is recrystallized from ethanol-acetonitrile. Greyish crystals; M.P.=180° C.; Yield: 72%.

EXAMPLE 2

Preparation of 4-hydroxy-thieno[2,3-c]pyridine

Derivative No. 2, (I): $R_1=R_2=H$ (a) Preparation of 4-hydroxy-6-tosyl-4,5,6,7-tetrahydro thieno[2,3-c]pyridine (V): $R_1=R_2=H$; $R_3=$p-tolyl This compound is prepared according to the procedure of Example 1(a), from 4-hydroxy-4,5,6,7-tetrahydro-thieno[2,3-c]pyridine hydrochloride. Beige crystals; M.p.=130° C. (isopropanol); Yield: 86%.

(b) Preparation of 4-oxo-6-tosyl-4,5,6,7-tetrahydro-thieno[2,3c]pyridine (III): $R_1=R_2=H$; $R_3=$p-tolyl This compound is prepared according to the procedure of Example 1(b), from the tosylate described in (a) above. Translucent white crystals; M.P.=172° C. (benzene); Yield: 98%.

(c) Preparation of 4-hydroxy-thieno[2,3-c]pyridine (I) $R_1=R_2=H$. Derivative No. 2

This compound is prepared according to the procedure of Example 1(c), from the tosylate described in (b) above (Yield: 78%). White crystals; M.p.=206° C. (ethanol-cyclohexane).

EXAMPLE 3

Preparation of 4-hydroxy-7-methyl-thieno[2,3-c]pyridine (I)

Derivative No. 3; $R_1=H$; $R_2=CH_3$ (a) Preparation of 4-hydroxy-7-methyl-6-tosyl-4,5,6,7-tetrahydro-thieno[2,3-c]pyridine (V): $R_1=H$; $R_2=CH_3$; $R_3=$p-tolyl.

This compound is prepared according to the procedure of Example 1(a), from 4-hydroxy-7-methyl-4,5,6,7-tetrahydro thieno[2,3-c]pyridine hydrochloride. Off-white crystals; M.p. 120° C. (benzene-cyclohexane). Yield: 96%.

(b) Preparation of 7-methyl-4-oxo-6-tosyl-4,5,6,7-tetrahydro-thieno[2,3-c]pyridine (III): $R_1=H$; $R_2=CH_3$; $R_3=$p-tolyl This compound is prepared according to the procedure of Example 1(b) from the tosylate described in (a) above. White crystals; M.p.=164° C. (benzene-acetone); Yield: 90%.

(c) Preparation of 4-hydroxy-7-methyl-thieno[2,3-c]pyridine (I)

$R_1=H$; $R_2=CH_3$. Derivative No. 3

This compound 6 is prepared according to the procedure of Example 1(c), from the tosylate described in (b) above. White crystals, M.p.=220° C. (cyclohexane-ethanol). Yield: 50%.

EXAMPLE 4

Preparation of 4-hydroxy-2-methyl-thieno[2,3-c]pyridine (I)

Derivative No. 4. $R_1=CH_3$; $R_2=H$

(a) Preparation of 4-hydroxy-2-methyl-6-tosyl-4,5,6,7-tetrahydro-thieno[2,3-c]pyridine (V): $R_1=CH_3$; $R_2=H$; $R_3=$p-tolyl This compound is prepared according to the procedure of Example 1(a), from 4-hydroxy-2-methyl-4,5,6,7-tetrahydro-thieno[2,3-c]pyridine hydrochloride (previously prepared). White crystals. M.p.=132° C. (benzene); Yield: 48%.

(b) Preparation of 2-methyl-4-oxo-6-tosyl-4,5,6,7-tetrahydro-thieno[2,3c-]pyridine (III): $R_1=CH_3$; $R_2=H$; $R_3=$p-tolyl.

This compound is prepared according to the procedure of Example 1(b), from the tosylate described in (a) above. Off-white crystals; M.p. 124° C. Yield: 83%.

(c) Preparation of 4-hydroxy-2-methyl-thieno[2,3-c]-pyridine (I)

$R_1=CH_3$; $R_2=H$. Derivative No. 4

This compound is prepared according to the procedure of Example 1(c), from the tosylene described in (b) above. Greyish crystals; M.p.=220° C. (ethanol-acetonitrile); Yield: 36%.

EXAMPLE 5

Preparation of 4-hydroxy-thieno[2,3-c]pyridine Derivative No. 2

This Example is a modification of the process for the preparation of Derivative No. 2 illustrated in Example 2.

(a) Preparation of 4-hydroxy-6-mesyl-4,5,6,7-tetrahydro thieno[2,3-c]pyridine (V): $R_1=R_2=H$; $R_3=CH_3$ To a mixture of 4-hydroxy-4,5,6,7-tetrahydro-thieno-[2,3-c]pyridine hydrochloride (50 g; 0.26 mole), chloroform (200 ml) and saturated aqueous potassium carbonate solution (100 ml) is added dropwise a solution of methanesulfonyl chloride (30 g; 0.26 mole) in chloroform (50 ml), at room temperature and with vigorous mechanical stirring. Stirring is continued a further 2 hours at room temperature. After decantation, the chloroform phase is washed with dilute hydrochloric acid, then with water, and is dried over anhydrous sodium sulfate. Evaporation of the solvent, in vacuo, leaves crystals which are recrystallized from methanol. Light brown crystals; M.p.=140° C. (methanol); Yield: 76%.

(b) Preparation of 6-mesyl-4-oxo-4,5,6,7-tetrahydrothieno[2,3-c]pyridine (III): $R_1=R_2=H$; $R_3=CH_3$ This compound is prepared according to the procedure of Example 1(b), from the methane sulfonate described in (a) above. Beige crystals, M.p.=120° C. (isopropanol-ethyl acetate); Yield: 70%.

(c) Preparation of 4-hydroxy-thieno[2,3-c]pyridine (I) $R_1=R_2=H$

This compound is prepared according to the procedure of Example 1(c), from the methanesulfonate described in (b) above (Yield: 80%). White crystals; M.p.=206° C. (ethanol-cyclohexane)

The results of toxicological and pharmacological tests reported below demonstrate the useful activities of the derivatives of the formulae (I) and/or (II), typically their anti-inflammatory activities.

Thus, this invention includes also within its scope a therapeutic composition having, in particular, anti-inflammatory activities, comprising, as active ingredient, an efficient amount of a derivative of the formula (I) and/or a pharmaceutically acceptable acid addition salt thereof, together with usual carriers and excipients.

I—Toxicological Investigation

The compounds of this invention benefit from an excellent tolerance and a low toxicity. Thus, the $LD_{50}/24$ hrs/kg body weight of animals, determined in mice according to the method of Miller & Tainter, by the oral route, is in excess of 800 mg for all derivatives.

By the intravenous route, for illustrative purposes, the $LD_{50}$ determined in mice is 131 mg for Derivative No. 1.

In addition, the tests effected on acute toxicity, chronic toxicity, sub-chronic toxicity and delayed toxicity in various animal species failed to disclose any local or systemic reaction, any perturbation in the regularly effected biological controls, and any anomaly in the microscopic and macroscopic examinations effected in the animals sacrificed and autopsied at the end of the experimentation.

II—Pharmacological Investigation

The pharmacological investigation concerned the anti-inflammatory activity of the compounds of this invention. This activity was investigated according to 2 methods:

(a) Method of localized carrageenin-induced edema

An 1% (0.1 ml) carrageenin solution is injected in the metatarsal flexor muscles of the right hind limb of rats at time 0. The animals of the treated group are additionally administered orally 100 mg/kg body weight of the test derivative, respectively 1 hour prior to injection of the phlogogenic agent, simultaneously with said injection, and then 1 and 2.5 hours thereafter. The determinations effected with a ROCH micrometer at times 0, 1 hour 2 hrs, 3 hrs and 5 hrs after carrageenin administration provide a measure, as a function of time, of the percent anti-inflammatory activity, with respect to the reference group.

The results thus obtained are set forth in following Table I.

TABLE I

| Derivative n° | Percent anti-inflammatory activity after | | | |
|---|---|---|---|---|
| | 1 hr | 2 hrs | 3 hrs | 5 hrs |
| 1 | 43 | 46 | 48 | 49 |
| 2 | 40 | 45 | 49 | 49 |
| 3 | 42 | 48 | 52 | 51 |
| 4 | 45 | 49 | 50 | 52 |

(b) Method of the ovalbumin-induced systemic edema

A simultaneous intraperitoneal injection of 1 ml ovalbumin and 0,5 ml of 1% aqueous Evans blue solution is effected in rats. On the other hand, the animals of the treated group are orally administered 100 mg/kg body weight of the test derivative, 1 hour prior to ovalbumin administration and simultaneously therewith. The intensity of the phenomenon thus induced is rated according to a scale from 1 to 5, according to the progress of the inflammatory syndrome. Thus are determined, as a function of time, the mean intensity of the edema and the percent decrease of the edema reaction with respect to the reference group. The percent anti-inflammatory activity obtained 2 hrs and 3 hrs after ovalbumin injection is set forth in following Table II:

TABLE II

| Derivative n° | Percent anti-inflammatory activity after | |
|---|---|---|
| | 2 hrs | 3 hrs |
| 1 | 44 | 50 |
| 2 | 49 | 58 |
| 3 | 53 | 61 |
| 4 | 48 | 60 |

The results of said investigations demonstrate the low toxicity and the valuable anti-inflammatory properties of the derivatives of this invention, which make them highly useful in human and veterinary medicine.

The therapeutic composition of this invention may be formulated, for oral administration, as tablets, coated tablets, capsules, drops ans syrups. It may also be formulated, for rectal administration, as suppositories and, for parenteral administration, as injectable solutions.

Each unit dose contains advantageously 0.010–0.250 g active ingredient, the daily dosage regimen varying from 0.010 g to 0.750 g active ingredient, according to the age of the patient and the condition treated.

Non-limiting Examples of therapeutic compositions containing compounds of this invention are given below:

1. Tablets

Derivative No. 2. . . . 0.100 g
Excipient: wheat starch, lactose, gum arabic, silica, magnesium stearate

2. Coated tablets

Derivative No. 4. . . . 0.075 g
Excipient: talc, polyvinylpyrrolidone, magnesium stearate, calcium carbonate, shellac, gum arabic, sugar, titanium oxide, glucose, white wax, rosin, carnauba wax, lactose, sucrose, tartrazine yellow, patent blue.

3. Capsules

Derivative No. 3. . . . 0.150 g
Excipient: talc, corn starch, stearic acid

4. Injectable ampoules

Derivative No. 2. . . . 0.100 g
Excipient: isotonic solution, sufficient to make 5 ml

5. Suppositories

Derivative No. 4. . . . 0.100 g
Excipient: semi-synthetic triglycerides.

The good tolerance of the derivatives of this invention, together with their substantial anti-inflammatory activities, are apparent from the above toxicological and pharmacological investigations.

Thus, the therapeutic composition of this invention may profitably be administered to humans in the treatment of any inflammatory conditions, whatever their etiology: chronic inflammatory rheumatism; degenerative rheumatism; ab-articular conditions; inflammatory conditions of the oto-rhino-laryngologic area; in traumatology; in odontostomatology; in post-operative surgery and in gynecology.

Having now described our invention what we claim as new and desire to secure by Letters Patent is:

1. A thieno(2,3-c)pyridine compound of the formula

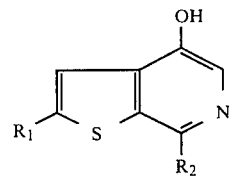

2. The derivative of claim 1, wherein the alkyl is a $C_{1-6}$ lower alkyl, or a pharmaceutically acceptable acid addition salt thereof.

3. A thieno-pyridine of claim 1 selected from the group consisting of:
4-hydroxy-thieno(2,3-c)pyridine,
4-hydroxy-2-methyl-thieno(2,3-c)pyridine,
4-hydroxy-7-methyl-thieno(2,3-c)pyridine
or a pharmaceutically acceptable acid addition salt thereof.

4. The compound of claim 1
4-hydroxy-thieno(2,3-c)pyridine or a pharmaceutically acceptable acid addition salt thereof.

5. The compound of claim 1
4-hydroxy-2-methyl-thieno(2,3-c)pyridine or a pharmaceutically acceptable acid addition salt thereof.

6. The compound of claim 1
4-hydroxy-7-methyl-thieno(2,3-c)pyridine or a pharmaceutically acceptable acid addition salt thereof.

7. An anti-inflammatory composition comprising a pharmaceutically acceptable carrier, and in an effective amount, a compound selected from the group consisting of thieno(2,3-c)pyridine of the formula

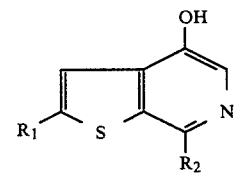

in which $R_1$ and $R_2$, which may be the same or different represent hydrogen or loweralkyl, and the pharmaceutically acceptable acid addition salts thereof. in which $R_1$ and $R_2$ which may be the same or different represent hydrogen or loweralkyl group, or a pharmaceutically acceptable acid addition salt thereof.

8. The therapeutic composition of claim 7, in unit dosage form, in which the effective amount is about 10–250 mg active ingredient.

9. The composition of claim 7 wherein the active ingredient is selected from the group consisting of:
4-hydroxy-thieno(2,3-c)pyridine,
4-hydroxy-2-methyl-thieno(2,3-c)pyridine,
4-hydroxy-7-methyl-thieno(2,3-c)pyridine
and the pharmaceutically acceptable acid addition salts thereof.

10. The composition of claim 7 wherein the active ingredient is 4-hydroxy-thieno(2,3-c)pyridine or a pharmaceutically acceptable acid addition salt thereof.

11. The composition of claim 7 wherein the active ingredient is 4-hydroxy-2-methyl-thieno(2,3-c)pyridine or a pharmaceutically acceptable acid addition salt thereof.

12. The composition of claim 7 wherein the active ingredient is 4-hydroxy-7-methyl-thieno(2,3-c)pyridine, or a pharmaceutically acceptable acid addition salt thereof.

13. A dosage unit comprising from about 0.010 to about 0.250 g of a composition of claim 10, 11, 12 or 7 including a pharmaceutically acceptable carrier.

14. A method for the treatment of inflammatory conditions in warm-blooded animals which comprises administering to a warm blooded animal an amount effective for that purpose of a substance selected from the group consisting of thieno(2,3-c)pyridine of the formula

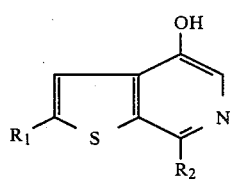

in which $R_1$ and $R_2$, which may be the same of different, represent hydrogen or a loweralkyl group, and the pharmaceutically acceptable acid addition salts thereof.

15. The method of claim 14 wherein the subtance is selected from the group consisting of
   4-hydroxy-thieno(2,3-c)pyridine,
   4-hydroxy-2-methyl-thieno(2,3-c)pyridine,
   4-hydroxy-7-methyl-thieno(2,3-c)pyridine or a pharmaceutically acceptable acid addition salt thereof.

16. The method of claim 14 wherein the substance is 4-hydroxy-thieno(2,3-c)pyridine or a pharmaceutically acceptable acid addition salt thereof.

17. The method of claim 14 wherein the substance is 4-hydroxy-2-methyl-thieno(2,3-c)pyridine or a pharmaceutically acceptable acid addition salt thereof.

18. The method of claim 14 wherein the substance is 4-hydroxy-7-methyl-thieno(2,3-c)pyridine or a pharmaceutically acceptable acid addition salt thereof.

19. The method of claim 16, 17, 18 or 14 wherein the substance is administered in a daily dosage of from about 0.010 to about 0.750 g of the active ingredient.

20. The method of claim 19 wherein the substance is administered in a unit dosage containing from about 0.010 to about 0.250 g of active ingredient.

21. The method of claim 14 wherein the substance is administered orally.

* * * * *